United States Patent
Hironaka et al.

(10) Patent No.: US 10,717,706 B2
(45) Date of Patent: Jul. 21, 2020

(54) M-PHENYLENEDIAMINE COMPOUND AND METHOD FOR PRODUCING POLYMER COMPOUND USING SAME

(71) Applicant: FUJIFILM Corporation, Tokyo (JP)

(72) Inventors: Koji Hironaka, Kanagawa (JP); Shohei Kataoka, Kanagawa (JP); Masato Senoo, Kanagawa (JP); Tetsu Kitamura, Kanagawa (JP); Sotaro Inomata, Kanagawa (JP); Satoshi Sano, Kanagawa (JP); Masatoshi Yumoto, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 16/274,246

(22) Filed: Feb. 13, 2019

(65) Prior Publication Data
US 2019/0177270 A1   Jun. 13, 2019

Related U.S. Application Data

(63) Continuation of application No. PCT/JP2017/025347, filed on Jul. 12, 2017.

(30) Foreign Application Priority Data

Aug. 31, 2016   (JP) .................. 2016-168767

(51) Int. Cl.
*C07C 311/44* (2006.01)
*C07C 311/39* (2006.01)
(Continued)

(52) U.S. Cl.
CPC .......... *C07C 311/44* (2013.01); *C07C 311/39* (2013.01); *C07C 311/43* (2013.01);
(Continued)

(58) Field of Classification Search
None
See application file for complete search history.

(56) References Cited

U.S. PATENT DOCUMENTS 4,496,491 A    1/1985   Kopp et al.
2014/0352534 A1   12/2014   Sano et al.
(Continued)

FOREIGN PATENT DOCUMENTS

JP   S5826853   2/1983
JP   2015083296   4/2015
(Continued)

OTHER PUBLICATIONS

"Written Opinion of the International Searching Authority (Form PCT/ISA/237) of PCT/JP2017/025347," dated Sep. 12, 2017, with English translation thereof, pp. 1-8.
(Continued)

*Primary Examiner* — Amy C Bonaparte
(74) *Attorney, Agent, or Firm* — JCIPRNET

(57) ABSTRACT

An m-phenylenediamine compound is represented by the following General Formula (I), (II), or (III).

General Formula (I)

(Continued)

-continued

General Formula (II)

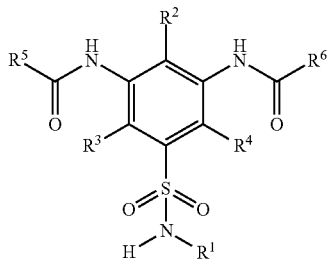

General Formula (III)

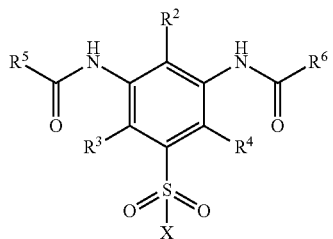

R¹ represents a hydrogen atom, an alkyl group, a cycloalkyl group, or an aryl group. R², R³, and R⁴ each represent an alkyl group. R⁵ and R⁶ each represent an alkyl group. X represents a chlorine atom or a bromine atom. A method for producing a polymer compound includes obtaining a polymer compound by using the m-phenylenediamine compound represented by General Formula (I) as a raw material.

9 Claims, 1 Drawing Sheet

(51) Int. Cl.
C08G 69/26 (2006.01)
C07F 5/02 (2006.01)
C08G 73/10 (2006.01)
C08G 69/42 (2006.01)
C08G 18/38 (2006.01)
C07C 311/43 (2006.01)
C07C 303/38 (2006.01)

(52) U.S. Cl.
CPC ............ *C07F 5/025* (2013.01); *C08G 18/387* (2013.01); *C08G 18/3861* (2013.01); *C08G 69/26* (2013.01); *C08G 69/42* (2013.01); *C08G 73/10* (2013.01); *C08G 73/1064* (2013.01); *C07C 303/38* (2013.01)

(56) References Cited

U.S. PATENT DOCUMENTS

| 2016/0199790 A1 | 7/2016 | Usami et al. |
| 2018/0085716 A1 | 3/2018 | Hironaka et al. |
| 2019/0076777 A1* | 3/2019 | Mochizuki ............. B01D 71/40 |

FOREIGN PATENT DOCUMENTS

| JP | 2015160167 | 9/2015 |
| WO | 2013122152 | 8/2013 |
| WO | 2015129554 | 9/2015 |
| WO | 2017002407 | 1/2017 |

OTHER PUBLICATIONS

"International Search Report (Form PCT/ISA/210) of PCT/JP2017/025347," dated Sep. 12, 2017, with English translation thereof, pp. 1-5.

\* cited by examiner

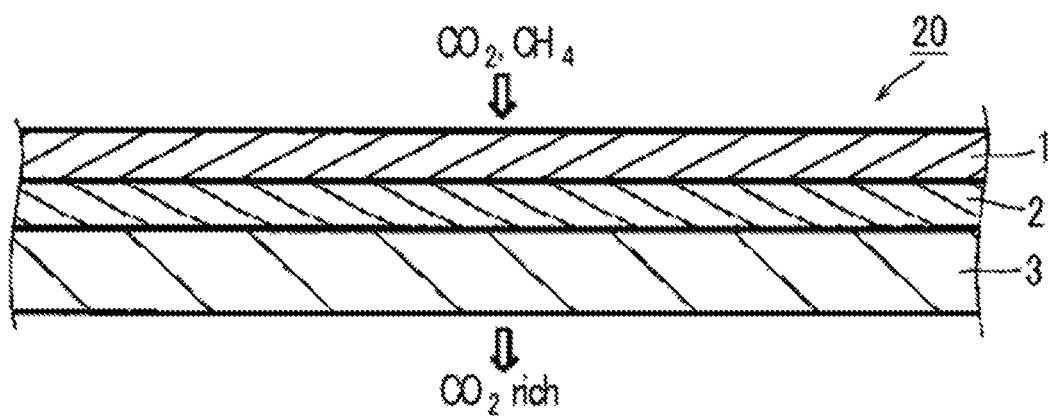

M-PHENYLENEDIAMINE COMPOUND AND METHOD FOR PRODUCING POLYMER COMPOUND USING SAME

CROSS-REFERENCE TO RELATED APPLICATIONS

This application is a Continuation of PCT International Application No. PCT/JP2017/025347, filed on Jul. 12, 2017, which claims priority under 35 U.S.C. § 119(a) to Japanese Patent Application No. 2016-168767, filed on Aug. 31, 2016. Each of the above application(s) is hereby expressly incorporated by reference, in its entirety, into the present application.

BACKGROUND OF THE INVENTION

1. Field of the Invention

The present invention relates to a novel m-phenylenediamine compound. The invention also relates to a method for producing a polymer compound using the novel m-phenylenediamine compound.

2. Description of the Related Art

Materials formed from polymer compounds have characteristic gas permeability, and these materials can separate a desired gas component by selectively permeating the gas component (for example, JP2015-160167A). Investigations are being conducted on separation and recovery of carbon dioxide from a large-sized source of carbon dioxide generation using a polymer membrane in thermal power stations, cement plants, blast furnaces in ironworks, and the like, by utilizing this characteristic of polymer materials. Furthermore, natural gas, biogases (gases generated as a result of fermentation and anaerobic digestion of excretions of living organisms, organic fertilizers, biodegradable materials, sewage water, rubbish, energy crops, and the like), and the like are mixed gases mainly including methane and carbon dioxide, and utilization of polymer membranes as means for removing impurities such as carbon dioxide from these mixed gases is under examination.

Phenylenediamine compounds are widely used as raw materials for the synthesis of various polymer compounds such as polyimides, polyurethanes, polyureas, and polyamides. For example, it is described in JP2015-160167A that a polyimide compound is obtained by subjecting a phenylenediamine compound having a carbamoyl group and a tetracarboxylic acid dianhydride having a particular structure to a polycondensation reaction, and that a membrane formed using this polyimide compound exhibits superior performance as a gas separation membrane that selectively permeates carbon dioxide from a mixed gas including carbon dioxide and methane. Furthermore, it is described in JP1983-026853A (JP-S58-026853A) that an amino group of an m-phenylenediamine having an N,N-disubstituted sulfonamide group is converted to isocyanate, and a polyurethane plastic is obtained by using this diisocyanate.

SUMMARY OF THE INVENTION

It is an object of the present invention to provide a novel m-phenylenediamine compound that is useful as a raw material for the synthesis of functional polymer compounds, or the like. Furthermore, it is another object of the invention to provide a method for producing a polymer compound using the above-described novel m-phenylenediamine compound.

The invention is configured to include the following technical means.

[1] An m-phenylenediamine compound represented by General Formula (I),

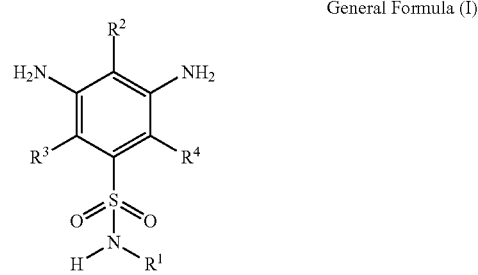

General Formula (I)

in the formula, $R^1$ represents a hydrogen atom, an alkyl group, a cycloalkyl group, or an aryl group; and $R^2$, $R^3$, and $R^4$ each represent an alkyl group.

[2] An m-phenylenediamine compound represented by General Formula (II),

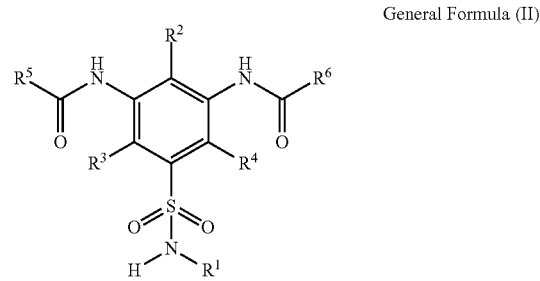

General Formula (II)

in the formula, $R^1$ represents a hydrogen atom, an alkyl group, a cycloalkyl group, or an aryl group; $R^2$, $R^3$, and $R^4$ each represent an alkyl group; and $R^5$ and $R^6$ each represent an alkyl group.

[3] The m-phenylenediamine compound according to <2>, wherein in General Formula (II), $R^5$ and $R^6$ each represent a trifluoromethyl group.

[4] An m-phenylenediamine compound represented by General Formula (III),

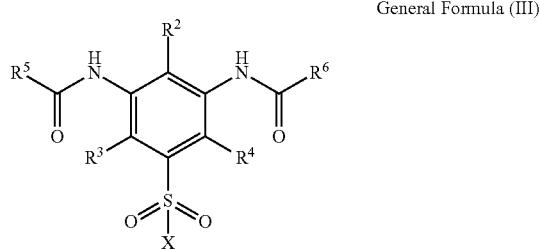

General Formula (III)

in the formula, $R^2$, $R^3$, and $R^4$ each represent an alkyl group; $R^5$ and $R^6$ each represent an alkyl group; and X represents a chlorine atom or a bromine atom.

[5] The m-phenylenediamine compound according to <4>, wherein in General Formula (III), $R^5$ and $R^6$ each represent a trifluoromethyl group.

[6] The m-phenylenediamine compound according to <4> or <5>, wherein in General Formula (III), X represents a chlorine atom.

[7] A method for producing a polymer compound, the method comprising obtaining a polymer compound by using the m-phenylenediamine compound according to <1> as a raw material.

[8] The method for producing a polymer compound according to <7>, wherein the polymer compound is a compound selected from a polyimide compound, a polyurethane compound, a polyurea compound, and a polyamide compound.

In the present specification, in a case in which there are a plurality of substituents, linking groups and the like (hereinafter, referred to as substituents and the like), which are represented by a particular reference symbol, or in a case in which a plurality of substituents and the like is to be defined simultaneously or selectively, it is meant that the respective substituents and the like may be identical with or different from each other. This also applies to the definition of the number of substituents and the like. Furthermore, in a case in which a plurality of substituents are disposed closely (particularly, adjacently), it is meant that those substituents may be linked or fused with one another and form a ring.

In regard to the indication of a compound in the present specification, the indication is used to mean the compound itself as well as a salt thereof and an ion thereof. To the extent that the desired effects are not impaired, the indication means to include a product obtained by changing a portion of the structure.

Examples of the salt of a compound include an acid addition salt of a compound, which is formed from the compound and an inorganic acid or an organic acid; and a base addition salt of a compound, which is formed from the compound and an inorganic base or an organic base. Examples of the ion of a compound include ions containing the skeleton of the compound, which is formed as a result of separation of a salt of the compound described above.

In regard to a substituent (similarly applicable also for a linking group) for which substitution or unsubstitution is not denoted in the present specification, it is meant that the group may have an optional substituent to the extent that desired effects are not impaired. This also applies to a compound for which substitution or unsubstitution is not denoted.

In a case in which merely the term "substituent" is mentioned in the present specification, unless particularly stated otherwise, the substituent may be a group selected from the Substituent Group Z that will be described below. Furthermore, in a case in which a substituent having a particular range is simply described (for example, in a case in which simply "alkyl group" is described), a preferred range and specific examples for a group corresponding to the following Substituent Group Z (in the above-described case, alkyl group) are applied.

In the present specification, in a case in which the number of carbon atoms of a certain group is to be defined, this number of carbon atoms means the number of carbon atoms in the entire group. That is, in a case in which this group further has a substituent, the number of carbon atoms means the number of carbon atoms of the entirety including this substituent.

In a case in which a substituent is mentioned in the present specification, unless particularly stated otherwise, the Substituent Group Z will be regarded as a preferred range of the substituent.

The m-phenylenediamine compound of the invention can be used as a raw material for the synthesis of a polymer compound, and desired characteristics can be imparted to the polymer compound to be obtained. For example, a polymer compound obtained by using the m-phenylenediamine compound of the invention as a raw material for synthesis (monomer) is such that various resin materials obtainable by producing the resin materials using this polymer compound can have physical properties with mutually contradictory characteristics, namely, flexibility and rigidity, which are appropriately well balanced. For example, in a case in which this polymer compound is used for a gas separation layer of a gas separation membrane, this gas separation membrane can be made to have gas permeability and gas separation selectivity balanced to a high level. Furthermore, this gas separation membrane is not likely to be plasticized and has excellent durability.

BRIEF DESCRIPTION OF THE DRAWINGS

The FIGURE is a cross-sectional view schematically illustrating a gas separation composite membrane produced in Examples.

DESCRIPTION OF THE PREFERRED EMBODIMENTS

The m-phenylenediamine compound according to the embodiment of the invention is represented by the following General Formula (I).

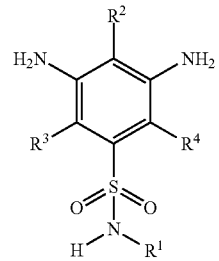

General Formula (I)

In General Formula (I), $R^1$ represents a hydrogen atom, an alkyl group, a cycloalkyl group, or an aryl group.

The alkyl group that can be employed as $R^1$ may be unsubstituted or may have a substituent. The alkyl group may also be a straight chain or may be branched. In a case in which the alkyl group that can be employed as $R^1$ has a substituent, this substituent may be, for example, a group selected from the Substituent Group Z that will be described below (provided that an alkyl group is excluded). Above all, this substituent is preferably a group selected from a halogen atom, an aryl group, an alkenyl group, an alkynyl group, a hydroxy group, an alkoxy group, an acyloxy group, an aryloxy group, an acylamino group, an amino group, an alkoxycarbonyl group, a carbamoyl group, a cyano group, an alkylsulfonyl group, an arylsulfonyl group, a sulfamoyl group, a carboxy group, a sulfo group, an acyl group, and a heterocyclic group; and particularly preferably a group selected from a halogen atom, a hydroxy group, a dialkylamino group, a carboxy group, and a sulfamoyl group.

In a case in which $R^1$ is an alkyl group, the number of carbon atoms of $R^1$ is preferably 1 to 12, more preferably 1 to 9, even more preferably 1 to 6, and particularly preferably 1 to 3. Specific examples of the alkyl group that can be employed as $R^1$ include, for example, unsubstituted methyl, unsubstituted ethyl, unsubstituted isopropyl, unsubstituted hexyl, unsubstituted dodecyl, allyl, propargyl, benzyl, carboxymethyl, carboxyethyl, carboxypentyl, methoxyethyl, hydroxyethyl, hydroxypropyl, mercaptoethyl, acetamidoethyl, dimethylaminoethyl, dimethylaminopropyl, trifluoroethyl, heptafluorobutyl, and undecafluorohexyl.

The alkyl group that can be employed as $R^1$ is preferably an unsubstituted alkyl group, an alkyl group having a carboxy group as a substituent (preferably, an alkyl group having one carboxy group as a substituent), or an alkyl group having a fluorine atom as a substituent.

The cycloalkyl group that can be employed as $R^1$ may be unsubstituted or may have a substituent. In a case in which the cycloalkyl group that can be employed as $R^1$ has a substituent, this substituent may be a group selected from the Substituent Group Z that will be described below. Above all, this substituent is preferably a group selected from a halogen atom, an aryl group, an alkenyl group, an alkynyl group, a hydroxy group, an alkoxy group, an acyloxy group, an aryloxy group, an acylamino group, an amino group, an alkoxycarbonyl group, a carbamoyl group, a cyano group, an alkylsulfonyl group, an arylsulfonyl group, a sulfamoyl group, a carboxy group, a sulfo group, an acyl group, and a heterocyclic group; and particularly preferably a group selected from a halogen atom, a hydroxy group, a dialkylamino group, a carboxy group, and a sulfamoyl group.

In a case in which $R^1$ is a cycloalkyl group, the number of carbon atoms of $R^1$ is preferably 3 to 12, more preferably 4 to 12, even more preferably 5 to 10, and still more preferably 6 to 10. Specific examples of the cycloalkyl group that can be employed as $R^1$ include, for example, unsubstituted cyclopropyl, unsubstituted cyclopentyl, unsubstituted cyclohexyl, 2-methylcyclohexyl, unsubstituted adamantyl, 4-hydroxycyclohexyl, and 4-carboxycyclohexyl.

The cycloalkyl group that can be employed as $R^1$ is preferably an unsubstituted cycloalkyl group or a cycloalkyl group having a carboxy group as a substituent (preferably, a cycloalkyl group having one carboxy group as a substituent).

The aryl group that can be employed as $R^1$ may be unsubstituted or may have a substituent. In a case in which the aryl group that can be employed as $R^1$ has a substituent, this substituent may be a group selected from the Substituent Group Z that will be described below. Above all, this substituent is preferably a group selected from a halogen atom, an alkyl group, an alkenyl group, an alkynyl group, a hydroxy group, an alkoxy group, an acyloxy group, an aryloxy group, an acylamino group, an amino group, an alkoxycarbonyl group, a carbamoyl group, a cyano group, an alkylsulfonyl group, an arylsulfonyl group, a sulfamoyl group, a carboxy group, a sulfo group, an acyl group, a dihydroxyboryl group, and a heterocyclic group; and particularly preferably a group selected from a halogen atom, an alkyl group, a hydroxy group, an acylamino group, a dialkylamino group, a carbamoyl group, a carboxy group, a sulfamoyl group, and a dihydroxyboryl group.

In a case in which $R^1$ is an aryl group, the number of carbon atoms of $R^1$ is preferably 6 to 18, more preferably 6 to 15, even more preferably 6 to 12, and particularly preferably 6 to 10. Specific examples of the aryl group that can be employed as $R^1$ include, for example, unsubstituted phenyl, naphthalen-1-yl, anthracen-9-yl, 2-methylphenyl, 2,6-dimethylphenyl, 2,4,6-trimethylphenyl, 4-tert-butylphenyl, 4-vinylphenyl, 2-allylphenyl, 4-ethynylphenyl, 2-phenylphenyl, 2-carboxyphenyl, 3-carboxyphenyl, 4-carboxyphenyl, 2-methoxyphenyl, 3-hydroxyphenyl, 4-hydroxyphenyl, 4-mercaptophenyl, 4-acetamidophenyl, 4-carbamoylphenyl, 4-sulfamoylphenyl, 4-dimethylaminophenyl, 3-dihydroxyborylphenyl, 3-trifluoromethylphenyl, 3,5-bis(trifluoromethyl)phenyl, 2,4-difluorophenyl, and 2,3,4,5,6-pentafluorophenyl.

The aryl group that can be employed as $R^1$ is preferably unsubstituted phenyl, a phenyl having a carboxy group as a substituent (preferably, a phenyl having one carboxy group as a substituent), a phenyl having a hydroxy group as a substituent (preferably, a phenyl having one hydroxy group as a substituent), a phenyl having a carbamoyl group as a substituent (preferably, a phenyl having one carbamoyl group as a substituent), a phenyl having a sulfamoyl group as a substituent (preferably, a phenyl having one sulfamoyl group as a substituent), a phenyl having a trifluoromethyl group as a substituent (preferably, a phenyl having two trifluoromethyl groups as substituents), a phenyl having a fluorine atom as a substituent (preferably, a phenyl having two fluorine atoms as substituents), or a phenyl having dihydroxyboryl as a substituent (preferably, a phenyl having one dihydroxyboryl as a substituent).

$R^1$ is more preferably a hydrogen atom, or a group selected from an unsubstituted alkyl group, an alkyl group having a carboxy group and/or a fluorine atom as a substituent, an unsubstituted phenyl group, and a phenyl group having a group selected from a carboxy group, a hydroxy group, a carbamoyl group, a sulfamoyl group, a trifluoromethyl group, a fluorine atom, and a dihydroxyboryl group as a substituent. $R^1$ is even more preferably a hydrogen atom, or a group selected from an unsubstituted alkyl group, an alkyl group having a fluorine atom as a substituent, unsubstituted phenyl, and a phenyl having a group selected from a carboxy group, a hydroxy group, a carbamoyl group, a sulfamoyl group, and a dihydroxyboryl group as a substituent. With consideration of production suitability, $R^1$ is particularly preferably a hydrogen atom.

$R^2$, $R^3$, and $R^4$ each represent an alkyl group. The alkyl group that can be employed as $R^2$, $R^3$, and $R^4$ may be unsubstituted or may have a substituent. Furthermore, this alkyl group may be a straight chain or may be branched. In a case in which the alkyl group that can be employed as $R^2$, $R^3$, and $R^4$ has a substituent, this substituent may be a group selected from the Substituent Group Z that will be described below (provided that an alkyl group is excluded). Above all, this substituent is preferably a group selected from a halogen atom, an aryl group, an alkoxy group, and an acylamino group; and particularly preferably a halogen atom or an acylamino group.

The number of carbon atoms of $R^2$, $R^3$, and $R^4$ is preferably 1 to 12, more preferably 1 to 9, even more preferably 1 to 6, and particularly preferably 1 to 3. Specific examples of $R^2$, $R^3$, and $R^4$ include, for example, unsubstituted methyl, unsubstituted ethyl, unsubstituted isopropyl, unsubstituted tert-butyl, unsubstituted hexyl, unsubstituted dodecyl, acetylaminomethyl, and trifluoromethyl.

$R^2$, $R^3$, and $R^4$ are each preferably an unsubstituted alkyl group, and particularly preferably unsubstituted methyl.

Specific examples of the m-phenylenediamine compound represented by General Formula (I) described above include the following; however, the invention is not intended to be limited to these specific examples. In the following specific examples, Me represents methyl, and Et represents ethyl.

1-1 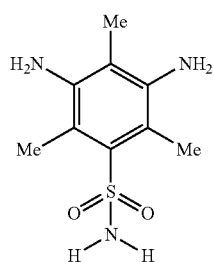
1-2 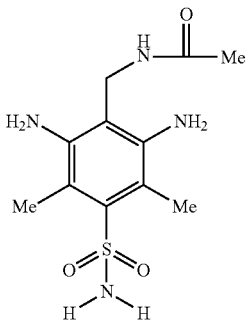
1-3 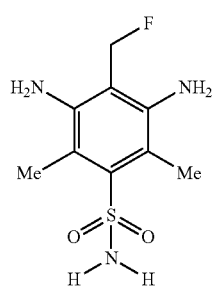
1-4 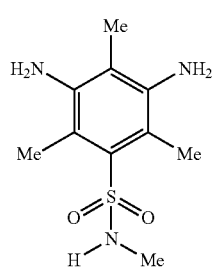
1-5 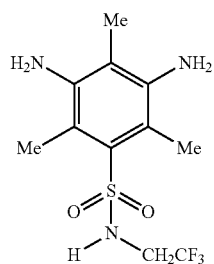
1-6 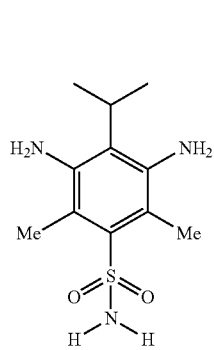
1-7 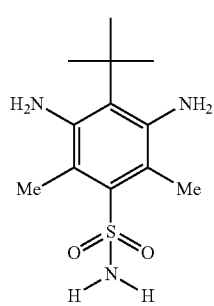
2-1 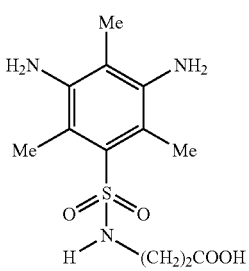
2-2
2-3

2-4
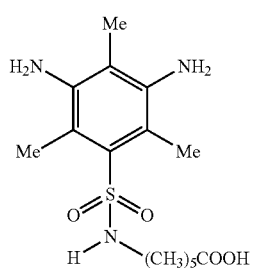
2-5
2-6
2-7
2-8
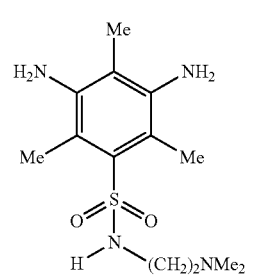
3-1
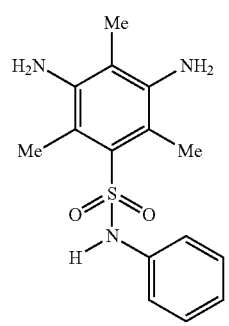
3-2
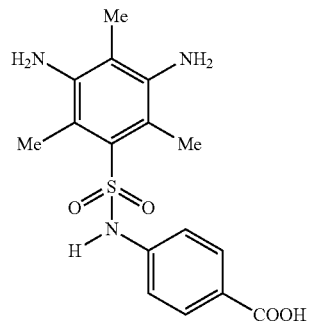
3-3
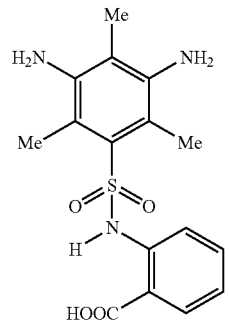
3-4
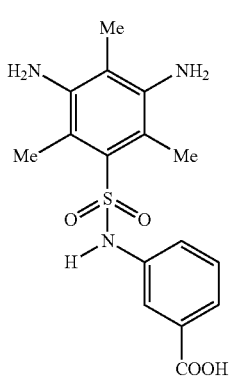

-continued
3-5
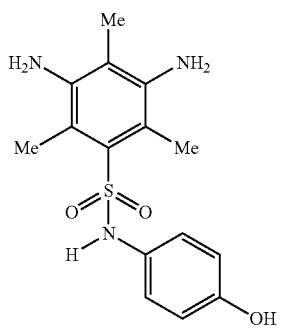
3-6
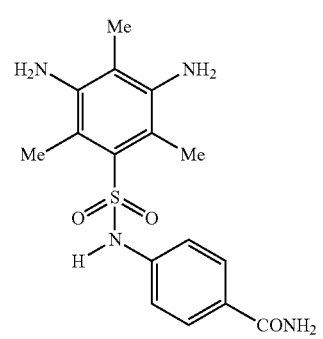
3-7
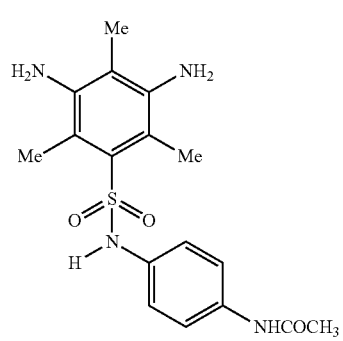
3-8
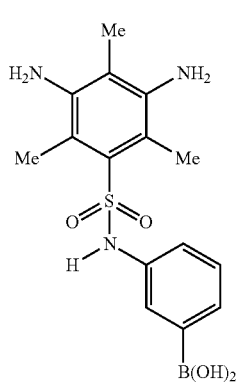
-continued
3-9
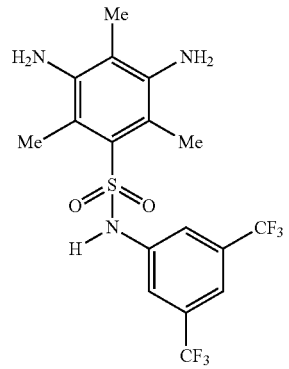
3-10
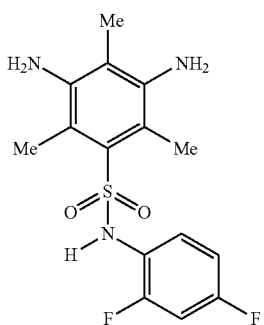
3-11
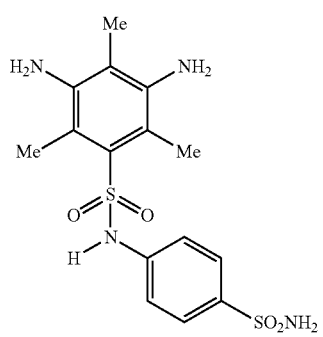
3-12
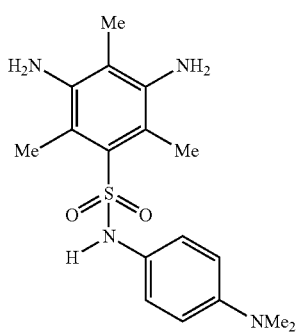
The method for obtaining the compound represented by General Formula (I) is not particularly limited. In regard to a synthesis reaction for obtaining the compound represented by General Formula (I), the reaction scheme according to a preferred embodiment will be shown below.

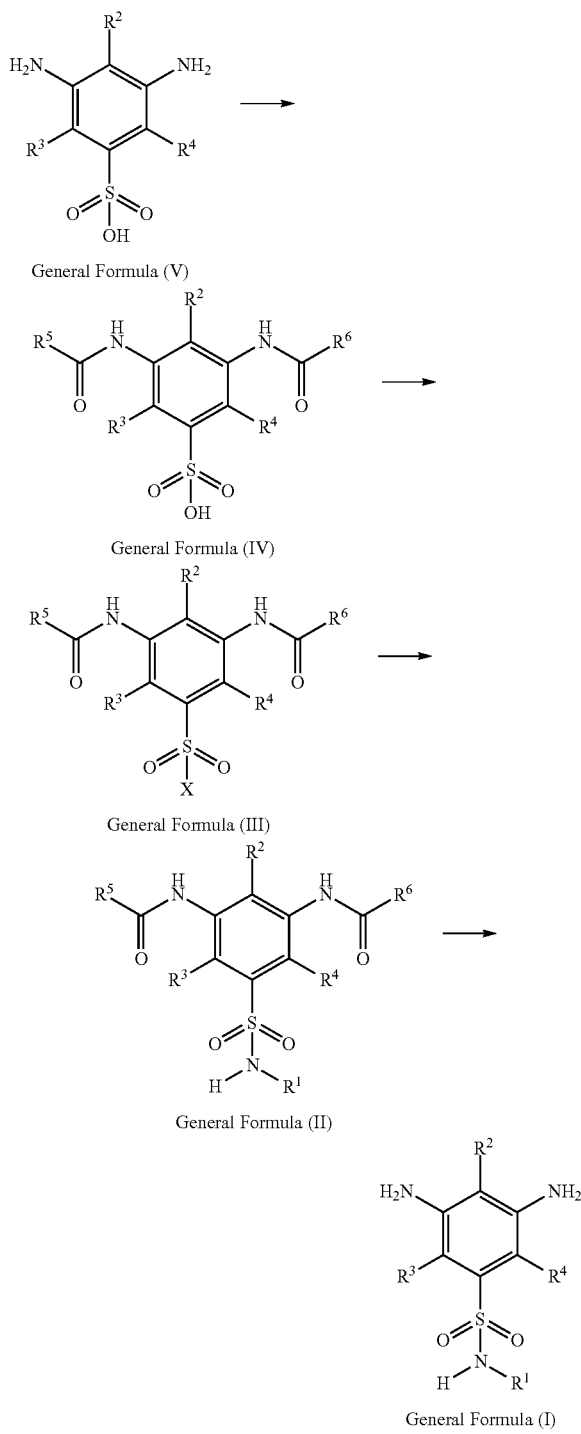

General Formula (V)

General Formula (IV)

General Formula (III)

General Formula (II)

General Formula (I)

An m-phenylenediamine compound represented by General Formula (IV) described above can be obtained by reacting an m-phenylenediamine compound represented by General Formula (V) described above with an acid anhydride and/or an acid halide (hereinafter, also referred to as "acylating agent") in the co-presence of a base (this reaction is referred to as "Reaction (V-IV)"). In General Formula (IV), $R^5$ and $R^6$ each represent an alkyl group (preferably, an alkyl group having 1 to 10 carbon atoms, more preferably 1 to 6 carbon atoms, and even more preferably 1 to 3 carbon atoms. This alkyl group may be linear or branched). The alkyl group represented by $R^5$ and $R^6$ may be unsubstituted or may have a substituent.

Regarding the acylating agent, for example, trifluoroacetic anhydride, acetyl chloride, acetic anhydride, and chloroacetyl chloride can be used. Among them, trifluoroacetic anhydride can be suitably used as the acylating agent, and in this case, $R^5$ and $R^6$ each become a trifluoromethyl group (—$CF_3$).

Regarding the base, for example, pyridine, triethylamine, dimethylaniline, and sodium hydroxide can be used. Above all, an organic base such as pyridine or triethylamine can be suitably used as the base, and it is particularly preferable to use pyridine.

For Reaction (V-IV), a solvent may also be used, and regarding this solvent, acetonitrile, ethyl acetate, and/or tetrahydrofuran can be suitably used. In the above-described scheme, the compound of General Formula (IV) is isolated as sulfonic acid; however, the compound can also be isolated as an organic base salt of sulfonic acid.

The reaction temperature for Reaction (V-IV) is preferably set to −10° C. to 80° C., and more preferably set to 5° C. to 70° C. The reaction time for Reaction (V-IV) is preferably set to 1 to 24 hours, and more preferably set to 2 to 12 hours. At the time point of reaction initiation for Reaction (V-IV), it is preferable that the concentration of the compound represented by General Formula (V) in the reaction liquid is set to 10 to 1,000 w/v %. Furthermore, at the time point of reaction initiation of Reaction (V-IV), the molar ratio of the acylating agent with respect to the compound represented by General Formula (V) (acylating agent/compound of General Formula (V)) is determined based on the stoichiometric ratio; however, the molar ratio is usually set to 2/1 to 10/1.

The compound represented by General Formula (V) can be synthesized by a conventional method, and it is also acceptable to use a commercially available product. Such a commercially available product can be purchased from, for example, Tokyo Chemical Industry Co., Ltd. and Wako Pure Chemical Industries, Ltd.

A reaction for obtaining an m-phenylenediamine compound represented by General Formula (III) from the m-phenylenediamine compound represented by General Formula (IV) (this reaction is referred to as "Reaction (IV-III)") is an acid halogenation reaction. X in General Formula (III) represents a chlorine atom or a bromine atom.

For this reaction, thionyl chloride, thionyl bromide, phosphorus oxychloride, or the like can be used as a halogenating agent, and it is particularly preferable to use thionyl chloride and/or phosphorus oxychloride.

In Reaction (IV-III), a solvent may be used, and regarding this solvent, acetonitrile, toluene, and/or chlorobenzene can be suitably used.

The reaction temperature for Reaction (IV-III) is preferably set to 5° C. to 120° C., and more preferably set to 20° C. to 80° C. The reaction time for Reaction (IV-III) is preferably set to 1 to 24 hours, and more preferably set to 2 to 12 hours. At the time point of reaction initiation of Reaction (IV-III), it is preferable that the concentration of the compound represented by General Formula (IV) in the reaction liquid is set to 10 to 1,000 w/v %. Furthermore, at the time point of reaction initiation of Reaction (IV-III), the molar ratio of the halogenating agent with respect to the compound represented by General Formula (IV) (halogenating agent/compound of General Formula (IV)) is determined based on the stoichiometric ratio; however, the molar ratio is usually set to 1/1 to 50/1.

A reaction for obtaining an m-phenylenediamine compound represented by General Formula (II) from the m-phenylenediamine compound represented by General Formula (III) (this reaction is referred to as "Reaction (III-II)") is a sulfonamidation reaction (sulfamoylation reaction). In this reaction, the m-phenylenediamine compound represented by General Formula (III) is reacted with an amine having a desired structure ($R^1NH_2$, wherein $R^1$ has the same meaning as $R^1$ in General Formula (I)) in the presence of a base. Furthermore, it is also acceptable to use an excess amount of $R^1NH_2$ without using a base.

In Reaction (III-II), a solvent may be used, and regarding this solvent, water, tetrahydrofuran, acetonitrile, and/or N-methylpyrrolidone is preferred.

The reaction temperature for Reaction (III-II) is preferably set to 0° C. to 100° C., and more preferably set to 5° C. to 80° C. The reaction time for Reaction (III-II) is preferably set to 1 to 24 hours, and more preferably set to 2 to 12 hours. At the time point of reaction initiation of Reaction (III-II), it is preferable that the concentration of the compound represented by General Formula (III) in the reaction liquid is set to 10 to 1,000 w/v %. Furthermore, at the time point of reaction initiation of Reaction (III-II), the molar ratio of $R^1NH_2$ with respect to the compound represented by General Formula (III) ($R^1NH_2$/compound of General Formula (III)) is determined based on the stoichiometric ratio; however, the molar ratio is usually set to 1/1 to 20/1.

A reaction for obtaining the m-phenylenediamine compound represented by General Formula (I) from the m-phenylenediamine compound represented by General Formula (II) (this reaction is referred to as "Reaction (II-I)") is a deprotection reaction. The conditions for this reaction are appropriately adjusted according to the reactivity of a protective group that has been introduced by reacting the m-phenylenediamine compound with an acylating agent in the above-described Reaction (V-IV). For example, in a case in which $R^5$ and $R^6$ are each a trifluoromethyl group, regarding the reaction conditions for the deprotection reaction, basic conditions may be adopted, or acidic conditions may be adopted. Examples of the base used in the case of adopting basic conditions include sodium hydroxide and potassium hydroxide. Examples of the acid used in the case of adopting acidic conditions include hydrochloric acid, sulfuric acid, methanesulfonic acid, and phosphoric acid.

It is preferable to use a solvent for Reaction (II-I), and regarding this solvent, water and/or an alcohol (methanol, ethanol, isopropanol, ethylene glycol, or the like) can be suitably used.

The reaction temperature for Reaction (II-I) is preferably set to 20° C. to 150° C., and more preferably set to 50° C. to 130° C. The reaction time for Reaction (II-I) is preferably set to 0.25 to 12 hours, and more preferably set to 0.5 to 8 hours. At the time point of reaction initiation of Reaction (II-I), it is preferable that the pH of the reaction liquid is set to 1 to 2, or 13 to 14.

There are no particular limitations on the use applications of the m-phenylenediamine compound represented by General Formula (I). For example, the compound can be used as a raw material for the synthesis of various polymer compounds. More particularly, a polyimide compound can be obtained by subjecting the m-phenylenediamine compound of General Formula (I) and a tetracarboxylic acid dianhydride to a polycondensation reaction. Synthesis of a polyimide compound can be carried out by a conventional method except for the raw materials to be used. Furthermore, a polyimide compound can be synthesized by referring to general textbooks (for example, Yoshio Imai and Rikio Yokota, ed., "Saishin Poriimido~Kiso to Oyo~(Latest Polyimides~Basics and Applications~)", NTS Publishing, Ltd., Aug. 25, 2010, p. 3-49).

Furthermore, a polyurethane compound can be obtained by converting an amino group of the m-phenylenediamine compound of General Formula (I) to isocyanate, and then reacting the compound with a diol compound. Synthesis of a polyurethane compound can be carried out by a conventional method, except for the raw materials to be used. For example, the Society of Polymer Science, Japan, Polymer Experimental Studies Editorial Committee, ed., "Kobunshi Jikkengaku Dai Go Kan Jushukugo to Jufuka (Polymer Experimental Studies, Vol. 5, Polycondensation and Polyaddition)", Kyoritsu Shuppan Co., Ltd., 1980, can be referred to.

A polyurea compound can be obtained by converting the m-phenylenediamine compound of General Formula (I) to isocyanate and then reacting the product with a diamine compound, or by reacting the m-phenylenediamine compound of General Formula (I) with a diisocyanate compound. Synthesis of a polyurethane compound can be carried out by a conventional method, except for the raw materials to be used. For example, the Society of Polymer Science, Japan, Polymer Experimental Studies Editorial Committee, ed., "Kobunshi Jikkengaku Dai Go Kan Jushukugo to Jufuka (Polymer Experimental Studies, Vol. 5, Polycondensation and Polyaddition)", Kyoritsu Shuppan Co., Ltd., 1980, can be referred to.

A polyamide compound can be obtained by subjecting the m-phenylenediamine compound of General Formula (I) and a dicarboxylic acid compound to a polycondensation reaction. Synthesis of a polyamide compound can be carried out by a conventional method, except for the raw materials to be used. For example, the Society of Polymer Science, Japan, Polymer Experimental Studies Editorial Committee, ed., "Kobunshi Jikkengaku Dai Go Kan Jushukugo to Jufuka (Polymer Experimental Studies, Vol. 5, Polycondensation and Polyaddition)", Kyoritsu Shuppan Co., Ltd., 1980, can be referred to.

A polymer compound obtained by using the m-phenylenediamine compound of General Formula (I) as a raw material is imparted with desired characteristics or functionality due to the characteristic structure possessed by the m-phenylenediamine compound of General Formula (I). For example, in a case in which a resin material is produced using a polymer compound synthesized by using the m-phenylenediamine compound of General Formula (I) as a raw material, this resin material can be properly imparted with two mutually contradictory characteristics, namely, flexibility and rigidity. The reason for this is not clearly understood; however, it is speculated that since all of $R^2$, $R^3$, and $R^4$ carried by a component derived from the m-phenylenediamine compound of General Formula (I) are alkyl groups, planarity and packing characteristics of the polymer compound can be properly suppressed. Meanwhile, another important reason is believed to be that the polymer compound is appropriately densified due to the action of a sulfamoyl group carried by a component derived from the m-phenylenediamine compound of General Formula (I), and mobility is properly suppressed.

Based on the characteristics described above, a polymer compound (preferably a polyimide compound) synthesized by using the m-phenylenediamine compound of General Formula (I) as a diamine raw material can be suitably used, for example, for a gas separation layer of a gas separation membrane. By using this polymer compound, even in a case in which a gas separation layer is formed into a thin layer, a desired gas component from a mixed gas can be permeated with high selectivity, and a balance between gas permeability and gas separation selectivity can be realized at a high level. Furthermore, this gas separation membrane is not likely to be plasticized even if exposed to impurity components such as toluene that exists in natural gas, and the gas separation membrane has excellent durability.

The reason for this is not clearly understood; however, as described above, the reason is considered to be as follows. As planarity and packing characteristics of the polymer compound are properly suppressed so that the free volume fraction becomes large; gas permeability is increased; and the polymer compound is appropriately densified as described above so that mobility is properly suppressed, permeability of molecules having a large dynamic molecule diameter can be effectively suppressed, and the interaction characteristics between a sulfamoyl group carried by a component derived from the m-phenylenediamine compound of General Formula (I) and a more plasticized component (toluene or the like) are effectively suppressed.

In regard to the application of a polymer membrane to a gas separation membrane, for example, JP2015-160166A and JP 2015-160167A can be referred to.

The description given above is intended to illustrate an example of the usefulness of the m-phenylenediamine compound of General Formula (I), and the use applications of the m-phenylenediamine compound of General Formula (I) are not to be limited by the description given above.

Substituent Group Z:

Examples include an alkyl group (preferably an alkyl group having 1 to 30 carbon atoms, more preferably 1 to 20 carbon atoms, even more preferably 1 to 10 carbon atoms, and particularly preferably 1 to 5 carbon atoms; examples include methyl, ethyl, isopropyl, tert-butyl, n-octyl, n-decyl, and n-hexadecyl), a cycloalkyl group (preferably a cycloalkyl group having 3 to 30 carbon atoms, more preferably 3 to 20 carbon atoms, and particularly preferably 3 to 10 carbon atoms; examples include cyclopropyl, cyclopentyl, and cyclohexyl), an alkylsulfonyl group, an arylsulfonyl group, a sulfo group, an alkenyl group (preferably an alkenyl group having 2 to 30 carbon atoms, more preferably 2 to 20 carbon atoms, even more preferably 2 to 10 carbon atoms, and particularly preferably 2 to 5 carbon atoms; examples include vinyl, allyl, 2-butenyl, and 3-pentenyl), an alkynyl group (preferably an alkynyl group having 2 to 30 carbon atoms, more preferably 2 to 20 carbon atoms, particularly preferably 2 to 10 carbon atoms, and particularly preferably 2 to 5 carbon atoms; examples include propargyl and 3-pentynyl), an aryl group (preferably an aryl group having 6 to 30 carbon atoms, more preferably 6 to 20 carbon atoms, and particularly preferably 6 to 12 carbon atoms; examples include phenyl, p-methylphenyl, naphthyl, and anthranyl), an amino group (including an amino group, an alkylamino group, an arylamino group, and a heterocyclic amino group, preferably an amino group having 0 to 30 carbon atoms, more preferably 0 to 20 carbon atoms, even more preferably 0 to 10 carbon atoms, and particularly preferably 0 to 6 carbon atoms; examples include amino, methylamino, dimethylamino, diethylamino, dibenzylamino, diphenylamino, and ditolylamino), an alkoxy group (preferably an alkoxy group having 1 to 30 carbon atoms, more preferably 1 to 20 carbon atoms, even more preferably 1 to 10 carbon atoms, and particularly preferably 1 to 5 carbon atoms; examples include methoxy, ethoxy, butoxy, and 2-ethylhexyloxy), an aryloxy group (preferably an aryloxy group having 6 to 30 carbon atoms, more preferably 6 to 20 carbon atoms, and particularly preferably 6 to 12 carbon atoms; examples include phenyloxy, 1-naphthyloxy, and 2-naphthyloxy), a heterocyclic oxy group (preferably a heterocyclic oxy group having 1 to 30 carbon atoms, more preferably 1 to 20 carbon atoms, and particularly preferably 1 to 12 carbon atoms; examples include pyridyloxy, pyrazyloxy, pyrimidyloxy, and quinolyloxy), an acyl group (preferably an acyl group having 1 to 30 carbon atoms, more preferably 1 to 20 carbon atoms, and particularly preferably 1 to 12 carbon atoms; examples include acetyl, benzoyl, formyl, and pivaloyl), an alkoxycarbonyl group (preferably an alkoxycarbonyl group having 2 to 30 carbon atoms, more preferably 2 to 20 carbon atoms, and particularly preferably 2 to 12 carbon atoms; examples include methoxycarbonyl and ethoxycarbonyl), an aryloxycarbonyl group (preferably an aryloxycarbonyl group having 7 to 30 carbon atoms, more preferably 7 to 20 carbon atoms, and particularly preferably 7 to 12 carbon atoms; examples include phenyloxycarbonyl), an acyloxy group (preferably an acyloxy group having 2 to 30 carbon atoms, more preferably 2 to 20 carbon atoms, and particularly preferably 2 to 10 carbon atoms; examples include acetoxy and benzoyloxy), an acylamino group (preferably an acylamino group having 2 to 30 carbon atoms, more preferably 2 to 20 carbon atoms, even more preferably 2 to 10 carbon atoms, and particularly preferably 2 to 5 carbon atoms; examples include acetylamino and benzoylamino), an alkoxycarbonylamino group (preferably an alkoxycarbonylamino group having 2 to 30 carbon atoms, more preferably 2 to 20 carbon atoms, and particularly preferably 2 to 12 carbon atoms; examples include methoxycarbonylamino), an aryloxycarbonylamino group (preferably an aryloxycarbonylamino group having 7 to 30 carbon atoms, more preferably 7 to 20 carbon atoms, and particularly preferably 7 to 12 carbon atoms; examples include phenyloxycarbonylamino), a sulfonylamino group (preferably having 1 to 30 carbon atoms, more preferably 1 to 20 carbon atoms, and particularly preferably 1 to 12 carbon atoms; examples include methanesulfonylamino and benzenesulfonylamino), a sulfamoyl group (preferably a sulfamoyl group having 0 to 30 carbon atoms, more preferably 0 to 20 carbon atoms, even more preferably 0 to 12 carbon atoms, and particularly preferably 0 to 6 carbon atoms; examples include sulfamoyl, methylsulfamoyl, dimethylsulfamoyl, and phenylsulfamoyl), a carbamoyl group (preferably a carbamoyl group having 1 to 20 carbon atoms, more preferably 1 to 16 carbon atoms, even more preferably 1 to 12 carbon atoms, and particularly preferably 1 to 7 carbon atoms; examples include a carbamoyl group, a methylcarbamoyl group, a diethylcarbamoyl group, and a phenylcarbamoyl group), an alkylthio group (preferably an alkylthio group having 1 to 30 carbon atoms, more preferably 1 to 20 carbon atoms, and particularly preferably 1 to 12 carbon atoms; examples include methylthio and ethylthio), an arylthio group (preferably an arylthio group having 6 to 30 carbon atoms, more preferably 6 to 20 carbon atoms, and particularly preferably 6 to 12 carbon atoms; examples include phenylthio), a heterocyclic thio group (preferably a heterocyclic thio group having 1 to 30 carbon atoms, more preferably 1 to 20 carbon atoms, and particularly preferably 1 to 12 carbon atoms; examples include pyridylthio, 2-benzimidazolylthio, 2-benzoxazolylthio, and 2-benzothiazolylthio), a sulfonyl group (preferably a sulfonyl group having 1 to 30 carbon atoms, more preferably 1 to 20 carbon atoms, and particularly preferably 1 to 12 carbon atoms; examples include mesyl and tosyl), a sulfinyl group (preferably a sulfinyl group having 1 to 30 carbon atoms, more preferably 1 to 20 carbon atoms, and particularly preferably 1 to 12 carbon atoms; examples include methanesulfinyl and benzenesulfinyl), a ureido group (preferably a ureido group having 1 to 30 carbon atoms, more preferably 1 to 20 carbon atoms, and particularly preferably 1 to 12 carbon atoms; examples include ureido, methylureido, and phenylureido), a phosphoric acid amide group (preferably a phosphoric acid amide group having 1 to 30 carbon atoms, more preferably 1 to 20 carbon atoms, and particularly preferably 1 to 12 carbon atoms; examples include diethylphosphoric acid amide and phenylphosphoric acid amide), a hydroxy group, a dihydroxyboryl group, a mercapto group, a halogen atom (examples include a fluorine atom, a chlorine atom, a bromine atom, and an iodine atom, and more preferably a fluorine atom), a cyano group, a carboxy group, an oxo group, a nitro group, a hydroxamic acid group, a sulfino group, a hydrazino group, an imino group, a heterocyclic group (preferably a heterocyclic group having a 3-membered to 7-membered ring, which may be an aromatic heterocyclic ring or a non-aromatic heterocyclic ring, and examples of the heteroatom that constitutes the heterocyclic ring include a nitrogen atom, an oxygen atom, and a sulfur atom. Preferably, a heterocyclic group having 0 to 30 carbon atoms and more preferably 1 to 12 carbon atoms; specific examples include imidazolyl, pyridyl, quinolyl, furyl, thienyl, piperidyl, morpholino, benzoxazolyl, benzimidazolyl, benzothiazolyl, carbazolyl, and azepinyl), a silyl group (preferably a silyl group having 3 to 40 carbon atoms, more preferably 3 to 30 carbon atoms, and particularly preferably 3 to 24 carbon atoms; examples include trimethylsilyl and triphenylsilyl), and a silyloxy group (preferably a silyloxy group having 3 to 40 carbon atoms, more preferably 3 to 30 carbon atoms, and particularly preferably 3 to 24 carbon atoms; examples include trimethylsilyloxy and triphenylsilyloxy). These substituents may be further substituted with any one or more substituents selected from the above-mentioned Substituent Group Z.

According to the invention, in a case in which a plurality of substituents exist at one structural site, those substituents may be linked to one another and form a ring, or the substituents may be fused with a portion or the entirety of the structural site and form an aromatic ring or an unsaturated heterocyclic ring.

In a case in which a compound, a substituent or the like includes an alkyl group, an alkenyl group, and the like, these may be linear or branched, and may be substituted or unsubstituted. In a case in which a compound, a substituent or the like includes an aryl group, a heterocyclic group, and the like, those may be monocyclic or fused cyclic, and may be substituted or unsubstituted.

In the present specification, in a case in which only the term "substituent" is described, unless particularly stated otherwise, the substituent refers to this Substituent Group Z. Furthermore, in a case in which only the name of each group described (for example, in a case in which only "alkyl group" is described), the preferred range and specific examples for the group corresponding to this Substituent Group Z are applicable.

The term "polymer compound" according to the invention is not particularly limited as long as the compound has a structure formed by two or more repeating units linked together, and the term is used to mean to include an oligomer and a polymer (meaning in a broader sense than conventional cases). The molecular weight of the polymer compound used for the invention is not particularly limited as long as the molecular weight satisfies the above-mentioned structure, and the molecular weight is preferably 1,000 to 1,000,000, more preferably 10,000 to 500,000, and even more preferably 20,000 to 300,000, as the weight-average molecular weight. Here, a molecular weight of 1,000 or more is a value as the weight-average molecular weight.

Unless particularly stated otherwise, the molecular weight and dispersibility according to the present specification are values measured using a GPC (gel permeation chromatography) method, and the molecular weight is defined as the weight-average molecular weight calculated relative to polystyrene standards. The gel packed in the columns used in the GPC method is preferably a gel having an aromatic compound in the repeating unit, and for example, a gel formed from a styrene-divinylbenzene copolymer may be used. Regarding the column, it is preferable to use two to six columns connected together. Examples of the solvent to be used include an ether-based solvent such as tetrahydrofuran; and an amide-based solvent such as N-methylpyrrolidinone. It is preferable that measurement is performed at a flow rate of the solvent in the range of 0.1 to 2 mL/min, and it is most preferable that measurement is performed at a flow rate of the solvent in the range of 0.5 to 1.5 mL/min. By performing measurement in this range, load is not applied on the apparatus, and measurement can be carried out more efficiently. Regarding the measurement temperature, it is preferable to perform measurement at 10° C. to 50° C., and it is most preferable to perform measurement at 20° C. to 40° C. The columns and carrier to be used can be selected as appropriate according to the physical properties of the polymer compound as an object of measurement.

EXAMPLES

Hereinafter, the present invention will be described in more detail by way of Examples; however, the invention is not intended to be limited to these Examples.

Synthesis Example m-Phenylene compounds shown in the following various Synthesis Examples were synthesized according to the following reaction scheme. In the respective Synthesis Examples described below, the number of the m-phenylenediamine compound corresponds to the number of the m-phenylenediamine compound of the above-mentioned example.

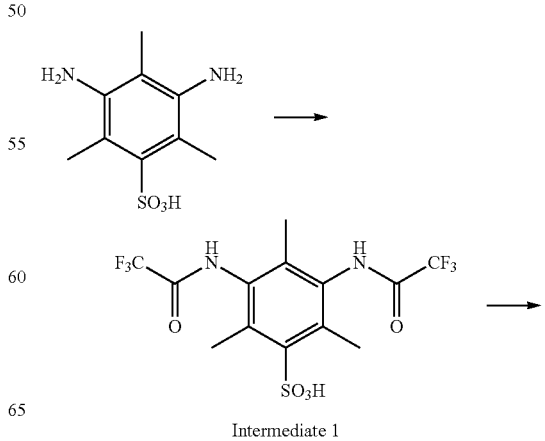

Intermediate 1

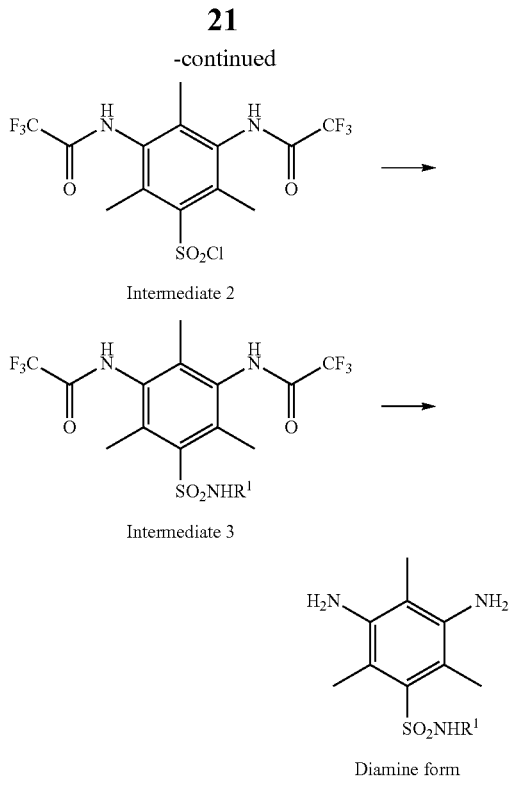

Intermediate 2

Intermediate 3

Diamine form

Synthesis Example 1 Synthesis of m-Phenylene Compound 1-1 (Wherein $R^1$ is a Hydrogen Atom)

(Synthesis of Intermediate 1)

Diaminomesitylenesulfonic acid (manufactured by Wako Pure Chemical Industries, Ltd.) (60 g), acetonitrile (manufactured by Wako Pure Chemical Industries, Ltd.) (380 g), and pyridine (manufactured by Wako Pure Chemical Industries, Ltd.) (23 g) were introduced into a 1-L flask. Next, trifluoroacetic anhydride (manufactured by Wako Pure Chemical Industries, Ltd.) (115 g) was carefully added dropwise to the flask under ice cooling, and then the mixture was allowed to react for 2 hours at 70° C. A solution thus obtained was cooled to room temperature, and then methanol (manufactured by Wako Pure Chemical Industries, Ltd.) (30 g) was added to the solution. The mixture was stirred for one hour. A solution thus obtained was concentrated under reduced pressure, and then the concentrate was purified using hydrochloric acid. Thus, Intermediate 1 (110 g) was obtained.

(Synthesis of Intermediate 2)

Acetonitrile (manufactured by Wako Pure Chemical Industries, Ltd.) (440 mL) and Intermediate 1 (68 g) were introduced into a 1-L flask. Next, thionyl chloride (manufactured by Wako Pure Chemical Industries, Ltd.) (115 g) and dimethylformamide (manufactured by Wako Pure Chemical Industries, Ltd.) (0.9 g) were carefully added to the flask, and then while caution was taken to prevent heat generation and foaming, the internal temperature was raised to 70° C. The mixture was stirred for 2 hours. A reaction liquid mixture thus obtained was distilled off under reduced pressure, and then the reaction mixture was purified by pouring onto ice. Thus, Intermediate 2 (65 g) was obtained.

$^1$H NMR (400 MHz, DMSO-$d^6$): δ=10.99 (brs, 1H), 10.96 (brs, 1H), 2.44 (s, 6H), 1.94 (s, 3H)

(Synthesis of Intermediate 3)

25% aqueous ammonia (manufactured by Wako Pure Chemical Industries, Ltd.) (90 g) was introduced into a 500-mL flask. Next, a liquid obtained by suspending Intermediate 2 (43 g) in tetrahydrofuran (manufactured by Wako Pure Chemical Industries, Ltd.) (130 g) was carefully added to the flask under ice cooling. A solution thus obtained was stirred for 2 hours at 40° C., and then the solution was concentrated under reduced pressure and purified. Thus, Intermediate 3 (30 g) in which $R^1$ is H was obtained.

$^1$H NMR (400 MHz, DMSO-$d^6$): δ=11.00 (brs, 1H), 10.96 (brs, 1H), 2.44 (s, 6H), 2.02 (s, 3H)

(Synthesis of m-Phenylene Compound 1-1)

Intermediate 3 (wherein $R^1$ is H) (30 g) and methanol (manufactured by Wako Pure Chemical Industries, Ltd.) (100 g) were introduced into a 200-mL flask. Next, methanesulfonic acid (manufactured by Wako Pure Chemical Industries, Ltd.) (30 g) was carefully added to the flask, and while caution was taken to prevent heat generation, the temperature was raised. The mixture was stirred for 30 minutes at 120° C. A reaction solution thus obtained was cooled, and then the reaction solution was poured into a potassium carbonate solution and then purified. Thus, m-phenylene compound 1-1 (11 g) was obtained. $^1$H NMR (400 MHz, DMSO-$d^6$): δ=6.93 (s, 2H), 4.09 (s, 4H), 2.25 (s, 6H), 1.94 (s, 3H)

Synthesis Example 2 Synthesis of m-Phenylene Compound 2-1 (Wherein $R^1$ is Methyl)

m-Phenylene compound 2-1 (10 g) was obtained in the same manner as in Synthesis Example 1, except that the aqueous ammonia used in the synthesis of Intermediate 3 in Synthesis Example 1 was replaced with a 40% aqueous solution of methylamine (38 g).

Intermediate 3 (Wherein $R^1$ is Methyl)

$^1$H NMR (400 MHz, DMSO-$d^6$): δ=11.22 (s, 1H), 11.17 (s, 1H), 7.66 (q, 1H), 2.51-2.44 (m, 9H), 2.04 (s, 3H)

m-Phenylene Compound 2-1

$^1$H NMR (400 MHz, DMSO-$d^6$): δ=6.89 (q, 1H), 4.49 (s, 4H), 2.34 (d, 3H), 2.25 (s, 6H), 1.95 (s, 3H)

Synthesis Example 3 Synthesis of m-Phenylene Compound 2-2 (Wherein $R^1$ is —$CH_2CF_3$)

m-Phenylene compound 2-2 (11 g) was obtained in the same manner as in Synthesis Example 1, except that the aqueous ammonia used in the synthesis of Intermediate 3 in Synthesis Example 1 was replaced with $CF_3CH_2NH_2$ (39 g).

Intermediate 3 (Wherein $R^1$ is —$CH_2CF_3$)

$^1$H NMR (400 MHz, DMSO-$d^6$): δ=11.23 (s, 1H), 11.18 (s, 1H), 8.88 (t, 1H), 3.88-3.76 (m, 2H), 2.45 (s, 6H), 2.04 (s, 3H)

Compound 2-2

$^1$H NMR (400 MHz, DMSO-$d^6$): δ=8.10 (s, 1H), 4.50 (s, 4H), 3.58-3.53 (m, 2H), 2.26 (s, 6H), 1.95 (s, 3H)

Synthesis Example 4 Synthesis of m-Phenylene Compound 3-1 (Wherein $R^1$ is Phenyl)

m-Phenylene compound 3-1 (13 g) was obtained in the same manner as in Synthesis Example 1, except that the aqueous ammonia used in the synthesis of Intermediate 3 in Synthesis Example 1 was replaced with $C_6H_5NH_2$ (45 g).

Intermediate 3 (Wherein $R^1$ is Phenyl)

$^1$H NMR (400 MHz, DMSO-d$^6$): δ=11.20 (brs, 1H), 11.14 (brs, 1H), 10.50 (brs, 1H), 7.23 (t, 2H), 7.06 (t, 1H), 6.98 (d, 2H), 2.45 (s, 6H), 2.02 (s, 3H)

Compound 3-1

$^1$H NMR (400 MHz, DMSO-d$^6$): δ=9.99 (s, 1H), 7.14 (t, 2H), 6.89 (m, 3H), 4.48 (brs, 4H), 2.29 (s, 6H), 1.91 (s, 3H)

Synthesis Example 5 Synthesis of m-Phenylene Compound 3-2 (Wherein $R^1$ is Carboxyphenyl)

m-Phenylene compound 3-2 (9 g) was obtained in the same manner as in Synthesis Example 1, except that the aqueous ammonia used in the synthesis of Intermediate 3 in Synthesis Example 1 was replaced with $C_6H_4(COOH)NH_2$ (53 g).

Intermediate 3 (Wherein $R^1$ is Carboxyphenyl)

$^1$H NMR (400 MHz, DMSO-d$^6$): δ=10.98 (brs, 1H), 10.92 (brs, 1H), 10.40 (brs, 1H), 7.79 (d, 2H), 7.03 (d, 2H), 2.44 (s, 6H), 2.02 (s, 3H)

Compound 3-2

$^1$H NMR (400 MHz, DMSO-d$^6$): δ=10.56 (s, 1H), 7.73 (d, 2H), 6.94 (d, 2H), 4.55 (brs, 4H), 2.31 (s, 6H), 1.91 (s, 3H)

Synthesis Example 6 Synthesis of m-Phenylene Compound 3-5 (Wherein $R^1$ is Hydroxyphenyl)

m-Phenylene compound 3-5 (15 g) was obtained in the same manner as in Synthesis Example 1, except that the aqueous ammonia used in the synthesis of Intermediate 3 in Synthesis Example 1 was replaced with $C_6H_4(OH)NH_2$ (50 g).

Intermediate 3 (Wherein $R^1$ is Hydroxyphenyl)

$^1$H NMR (400 MHz, DMSO-d$^6$): δ=11.18 (brs, 1H), 11.10 (brs, 1H), 9.84 (s, 1H), 9.41 (s, 1H), 6.81 (d, 2H), 6.60 (d, 2H), 2.32 (s, 6H), 2.01 (s, 3H)

Compound 3-5

$^1$H NMR (400 MHz, DMSO-d$^6$): δ=9.29 (s, 1H), 9.18 (s, 1H), 6.86 (d, 2H), 6.56 (d, 2H), 4.41 (s, 4H), 2.20 (s, 6H), 1.90 (s, 3H)

Synthesis Example 7 Synthesis of m-Phenylene Compound 3-6 (Wherein $R^1$ is Carbamoylphenyl)

m-Phenylene compound 3-6 (14 g) was obtained in the same manner as in Synthesis Example 1, except that the aqueous ammonia used in the synthesis of Intermediate 3 in Synthesis Example 1 was replaced with $C_6H_4(CONH_2)NH_2$ (55 g).

Intermediate 3 (Wherein $R^1$ is Carbamoylphenyl)

$^1$H NMR (400 MHz, DMSO-d$^6$): δ=11.21 (brs, 1H), 11.14 (brs, 1H), 10.80 (s, 1H), 7.82 (brs, 1H), 7.72 (d, 2H), 7.25 (brs, 1H), 6.97 (d, 2H), 2.49 (s, 6H), 2.02 (s, 3H)

Compound 3-6

$^1$H NMR (400 MHz, DMSO-d$^6$): δ=10.40 (brs, 1H), 7.67 (brs, 1H), 7.61 (d, 2H), 7.08 (brs, 1H), 6.83 (d, 2H), 4.45 (brs, 4H), 2.29 (s, 6H), 1.89 (s, 3H)

Synthesis Example 8 Synthesis of m-Phenylene Compound 3-8 (Wherein $R^1$ is Dihydroxyborylphenyl)

m-Phenylene compound 3-8 (8 g) was obtained in the same manner as in Synthesis Example 1, except that the aqueous ammonia used in the synthesis of Intermediate 3 in Synthesis Example 1 was replaced with $C_6H_4(B(OH)_2)NH_2$ (56 g).

Intermediate 3 (Wherein $R^1$ is Dihydroxyborylphenyl)

$^1$H NMR (400 MHz, DMSO-d$^6$): δ=11.21 (brs, 1H), 11.18 (brs, 1H), 10.36 (brs, 1H), 8.08 (brs, 2H), 7.54 (s, 1H), 7.50 (d, 1H), 7.19 (t, 1H), 7.00 (d, 1H), 2.43 (s, 6H), 2.01 (s, 3H)

Compound 3-8

$^1$H NMR (400 MHz, DMSO-d$^6$): δ=9.80 (s, 1H), 7.93 (s, 2H), 7.41 (s, 1H), 7.37 (d, 1H), 7.11 (t, 1H), 6.92 (d, 1H), 4.43 (brs, 4H), 2.29 (s, 6H), 1.89 (s, 3H)

Synthesis Example 9 Synthesis of m-Phenylene Compound 3-11 (Wherein $R^1$ is Sulfamoylphenyl)

m-Phenylene compound 3-11 (20 g) was obtained in the same manner as in Synthesis Example 1, except that the aqueous ammonia used in the synthesis of Intermediate 3 in Synthesis Example 1 was replaced with $C_6H_4(SO_2NH_2)NH_2$ (60 g).

Intermediate 3 (Wherein $R^1$ is Sulfamoylphenyl)

$^1$H NMR (400 MHz, DMSO-d$^6$): δ=11.21 (brs, 1H), 11.18 (brs, 1H), 11.12 (brs, 1H), 7.65 (d, 2H), 7.25 (s, 2H), 7.06 (d, 2H), 2.52 (s, 6H), 2.04 (s, 3H)

Compound 3-11

$^1$H NMR (400 MHz, DMSO-d$^6$): δ=10.60 (brs, 1H), 7.60 (d, 2H), 7.12 (brs, 2H), 6.98 (d, 2H), 4.51 (brs, 4H), 2.29 (s, 6H), 1.89 (s, 3H)

Synthesis Example 10 Synthesis of Polymer P-01

Polymer P-01 was synthesized according to the following scheme.

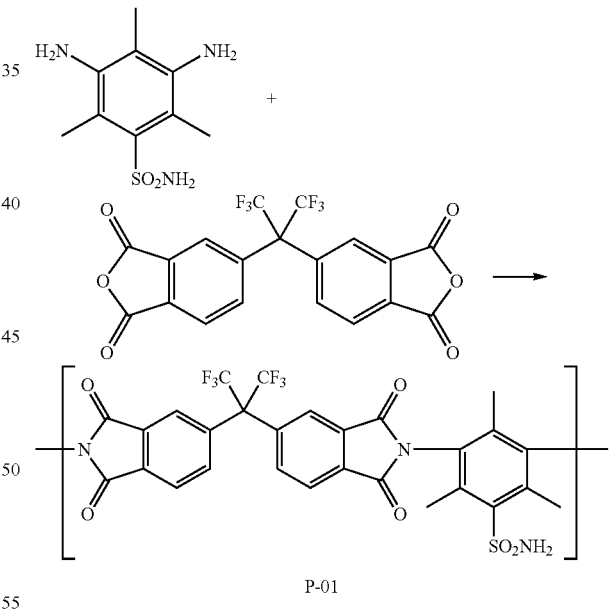

m-Cresol (manufactured by Wako Pure Chemical Industries, Ltd.) (100 g), m-phenylenediamine compound 1-1 (10.00 g) obtained in Synthesis Example 1, and 4,4'-(hexafluoroisopropylidene)diphthalic anhydride (6FDA, manufactured by Tokyo Chemical Industry Co., Ltd.) (19.37 g) were introduced into a 500-mL flask. Next, toluene (manufactured by Wako Pure Chemical Industries, Ltd.) (10 g) and isoquinoline (manufactured by Wako Pure Chemical Industries, Ltd.) (1.5 g) were added to the flask, and then the mixture was heated to 180° C. and was allowed to react for 6 hours. A solution thus obtained was cooled to room temperature (25° C.), and then the solution was diluted with acetone (manufactured by Wako Pure Chemical Industries, Ltd.). Subsequently, isopropyl alcohol (manufactured by Wako Pure Chemical Industries, Ltd.) was added thereto, and a polymer was obtained as a solid. Similar reprecipitation was repeated two times, and then the polymer was dried at 80° C. Thus, Polymer P-01 (24 g) was obtained.

Synthesis Examples 11 to 18 Synthesis of Polymers P-02 to P-09

Polymers P-02 to P-09 having the following structures were obtained in the same manner as in Synthesis Example 10, except that the various m-phenylenediamine compounds obtained in Synthesis Examples 2 to 9 were used instead of m-phenylenediamine compound 1-1 used in Synthesis Example 10.

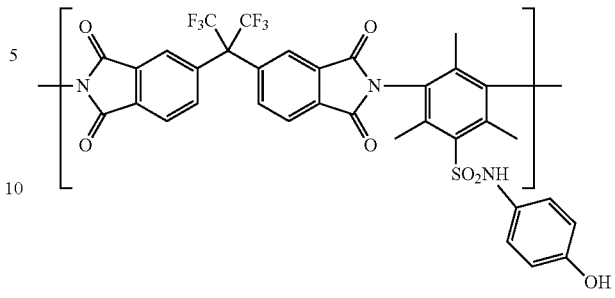

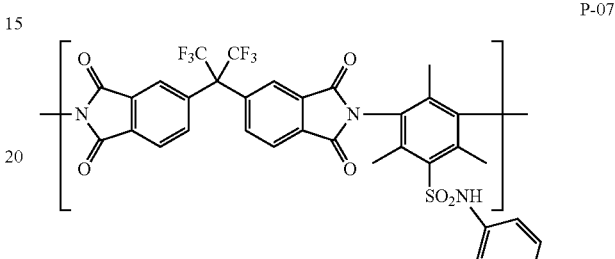

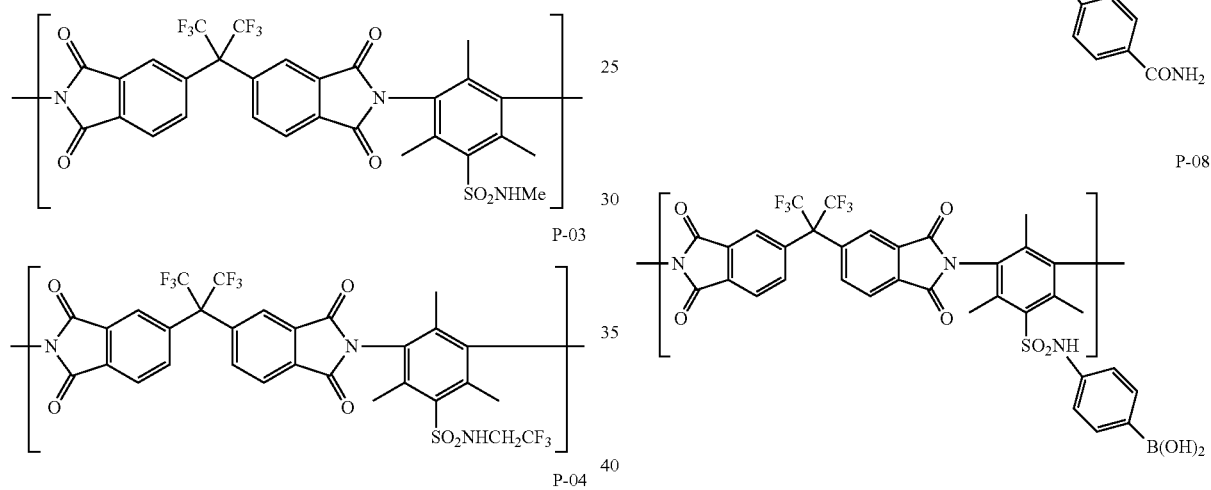

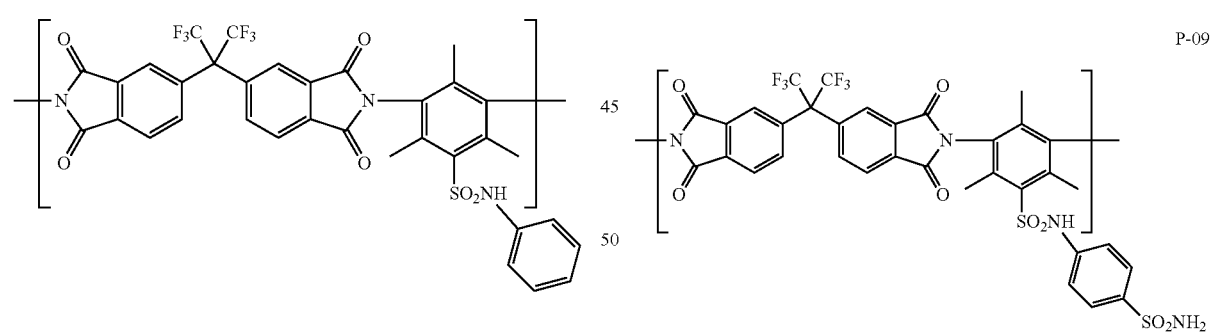

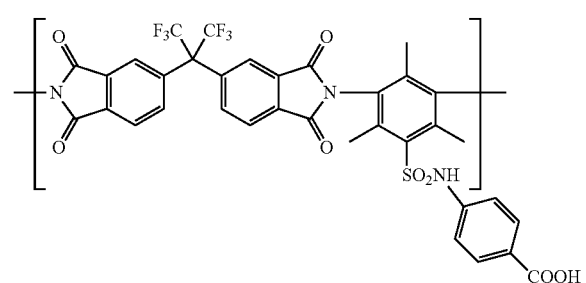

Comparative Synthesis Example 1 Synthesis of Comparative Polymer C-01

Comparative Polymer C-01 having the following structure was obtained in the same manner as in Synthesis Example 10, except that a compound having a structure in which two hydrogen atoms in a sulfamoyl group of m-phenylenediamine compound 1-1 had all been substituted by n-$C_4H_9$ was used instead of m-phenylenediamine compound 1-1 used in Synthesis Example 10.

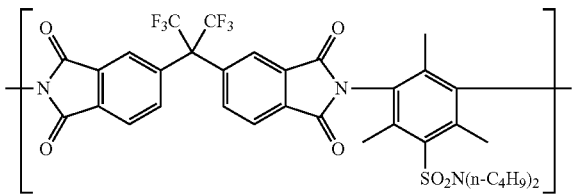

C-01

Comparative Synthesis Example 2 Synthesis of Comparative Polymer C-02

Comparative Polymer C-02 was obtained in the same manner as in the synthesis of Polymer P-01 described above, except that diaminomesitylenesulfonic acid (manufactured by Wako Pure Chemical Industries, Ltd.) was used instead of m-phenylenediamine compound 1-1 used in Synthesis Example 10, triethylamine (4.41 g) was added, and hydrochloric acid was used at the time of purification of the polymer.

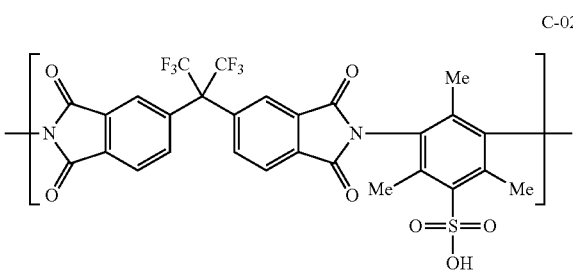

C-02

Comparative Synthesis Example 3 Synthesis of Comparative Polymer C-03

2,3,5,6-Tetramethyl-1,4-phenylenediamine (2.97 g) and N-methylpyrrolidone (50 mL) were introduced into a 300-mL flask. 6-FDA (manufactured by Tokyo Chemical Industry Co., Ltd.) (8.04 g) was added to the flask under ice cooling, and the mixture was washed in with N-methylpyrrolidone (6 mL). The mixture was stirred for 5 hours at 40° C., and then pyridine (manufactured by Wako Pure Chemical Industries, Ltd.) (0.43 g) and acetic anhydride (manufactured by Wako Pure Chemical Industries, Ltd.) (6.10 g) were added thereto. The reaction solution was heated to 80° C. and was stirred for 3 hours. The reaction solution was cooled, acetone was added thereto, and then methanol was added thereto. Thus, Comparative Polymer C-03 was precipitated as a powder. Methanol washing was repeated two times, and then the polymer was dried at 40° C. Thus, Comparative Polymer C-03 (9.32 g) was obtained.

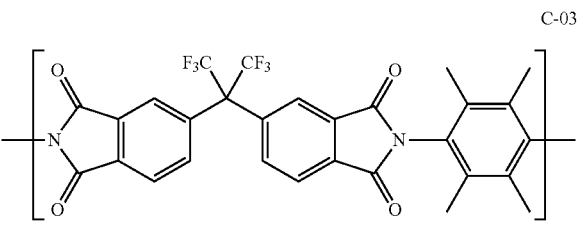

C-03

[Reference Example 1] Production of Composite Membrane

<Production of Smooth Layer-Attached PAN Porous Membrane>

(Production of Radiation-Curable Polymer Having Dialkylsiloxane Group)

39 g of UV9300 (manufactured by Momentive Performance Materials, Inc.), 10 g of X-22-162C (manufactured by Shin-Etsu Chemical Co., Ltd.), and 0.007 g of DBU (1,8-diazabicyclo[5.4.0]undec-7-ene) were introduced into a 150-mL three-necked flask, and the mixture was dissolved in 50 g of n-heptane. This was maintained at 95° C. for 168 hours, and thus a radiation-curable polymer solution having a poly(siloxane) group (viscosity at 25° C.: 22.8 mPa·s) was obtained.

(Production Polymerizable Radiation-Curable Composition)

5 g of the above-described radiation-curable polymer solution was cooled to 20° C. and was diluted with 95 g of n-heptane. To a solution thus obtained, 0.5 g of UV9380C (manufactured by Momentive Performance Materials, Inc.) and 0.1 g of ORGATIX TA-10 (manufactured by Matsumoto Fine Chemical Co., Ltd.), which are photopolymerization initiators, were added. Thus, a polymerizable radiation-curable composition was produced.

(Application of Polymerizable Radiation-Curable Composition on Porous Support, Formation of Smooth Layer)

A PAN (polyacrylonitrile) porous film (a polyacrylonitrile porous film exists on a nonwoven fabric, the film thickness including the nonwoven fabric is about 180 μm) was used as a support, and the above-described polymerizable radiation-curable composition was spin-coated thereon. Subsequently, the composition was subjected to a UV treatment (manufactured by Fusion UV Systems, Inc., Light Hammer 10, D-valve) under the UV treatment conditions of a UV intensity of 24 kW/m and a treatment time of 10 seconds, and then the composition was dried. In this manner, a smooth layer having a thickness of 1 μm and having a dialkylsiloxane group was formed on the porous support.

<Production of Composite Membrane>

A gas separation composite membrane 20 as illustrated in the FIGURE was produced. This gas separation composite membrane 20 has a gas separation layer 1 and a porous layer 2, as well as a nonwoven fabric layer 3 as a support layer. In the FIGURE, a smooth layer is not depicted in the diagram.

In a 30-ml brown vial, 0.08 g of Polymer P-01 and 7.92 g of tetrahydrofuran were mixed, and the mixture was stirred for 30 minutes. Subsequently, the mixture was spin-coated on the PAN porous film having a smooth layer formed thereon, and a gas separation layer was formed. Thus, a composite membrane was obtained. The thickness of the Polymer P-01 layer was about 100 nm, and the thickness of the polyacrylonitrile porous membrane including the nonwoven fabric was about 180 μm.

Regarding the molecular cutoff of such a polyacrylonitrile porous membrane, a porous membrane having a molecular cutoff of 100,000 or less was used. Furthermore, the carbon dioxide permeability of this porous membrane at 40° C. and 5 MPa was 25,000 GPU.

[Reference Examples 2 to 9] Production of Composite Membranes

Composite membranes were obtained in the same manner as in Reference Example 1, except that Polymers P-02 to P-09 were respectively used instead of Polymer P-01 of Reference Example 1.

[Comparative Reference Examples 1 to 3] Production of Composite Membranes

Composite membranes were obtained in the same manner as in Reference Example 1, except that Comparative Polymers C-01 to C-03 were respectively used instead of Polymer P-01 of Reference Example 1. Since Comparative Polymer C-02 did not dissolve in tetrahydrofuran, methanol was used instead of tetrahydrofuran.

[Test Example 1] Evaluation of $CO_2$ Permeation Rate and Gas Separation Selectivity of Composite Membrane-1

The gas separation performance was evaluated as follows using the composite membranes obtained in the various Reference Examples and Comparative Reference Examples. A composite membrane was cut out, together with the porous support (support layer), into a size with a diameter of 5 cm, and a permeation test sample was produced. A mixed gas of carbon dioxide ($CO_2$):methane ($CH_4$) of 6:94 (volume ratio) was supplied using a gas permeance measuring apparatus manufactured by GTR Tech Corporation, by regulating the mixed gas so as to have a total pressure on the gas supply side of 5 MPa (partial pressure of $CO_2$: 0.3 MPa), a flow rate of 500 mL/min, and a temperature of 30° C. The gas that had been permeated was analyzed by gas chromatography. A comparison of gas permeabilities of membranes was made by calculating the gas permeation rate as gas permeance. The unit for gas permeance (gas permeation rate) was expressed in the GPU unit [1 GPU=$1\times10^{-6}$ $cm^3$ (STP)/$cm^2 \cdot sec \cdot cmHg$]. Gas separation selectivity was calculated as the ratio of the permeation rate of $CO_2$, $R_{CO2}$, with respect to the permeation rate of $CH_4$, $R_{CH4}$ of the membrane ($R_{CO2}/R_{CH4}$).

[Test Example 2] Toluene Exposure Test

In a container made of stainless steel and holding a Petri dish on which toluene solvent was spread, a composite membrane produced in each of Reference Examples and Comparative Reference Examples was placed, and the container was tightly sealed. Subsequently, the system was stored for 10 minutes under the conditions of 25° C., and then similarly to [Test Example 1], the composite membrane was cut out into a size of a diameter of 5 cm. A permeation test sample was produced, and the gas separation performance was evaluated. The resistance to plasticization of a gas separation membrane against impurity components such as benzene, toluene, and xylene can be evaluated by exposure to toluene.

The results of the various Test Examples are presented in the following Table 1.

TABLE 1

| Type of polymer used in gas separation layer | Weight-average molecular weight of polymer used in gas separation layer | Test Example 1 | | Test Example 2 (after exposure to toluene) |
|---|---|---|---|---|
| | | $CO_2$ permeation rate | $R_{CO2}/R_{CH4}$ | $R_{CO2}/R_{CH4}$ |
| P-01 | 120,000 | 39 | 26 | 20 |
| P-02 | 100,000 | 45 | 22 | 15 |
| P-03 | 90,000 | 50 | 20 | 14 |
| P-04 | 120,000 | 44 | 23 | 16 |
| P-05 | 130,000 | 36 | 28 | 22 |
| P-06 | 120,000 | 35 | 27 | 21 |
| P-07 | 90,000 | 30 | 30 | 24 |
| P-08 | 150,000 | 30 | 28 | 22 |
| P-09 | 140,000 | 25 | 32 | 26 |
| C-01 | 120,000 | 50 | 15 | 5 |
| C-02 | 80,000 | (2000) | (1) | (1) |
| C-03 | 140,000 | 44 | 13 | 1 |

Comparative Polymer C-01 has a form in which the m-phenylenediamine component in the polymer has a sulfamoyl group, and two substituents carried by this sulfamoyl group have all been substituted. A composite membrane having a gas separation layer formed using this Comparative Polymer C-01 gave inferior results for gas separation selectivity ($R_{CO2}/R_{CH4}$). This composite membrane was likely to be plasticized by exposure to toluene and gave significantly inferior results concerning durability.

Comparative Polymer C-02 was not dissolved in tetrahydrofuran as described above and was dissolved in methanol. A film was formed by applying this solution. However, the gas separation layer thus obtained had many film defects and did not exhibit gas separation performance.

Comparative Polymer C-03 is such that the phenylenediamine component in the polymer does not have a sulfamoyl group. A composite membrane having a gas separation layer formed using this Comparative Polymer C-03 gave inferior results for gas separation selectivity ($R_{CO2}/R_{CH4}$). This composite membrane was likely to be plasticized by exposure to toluene and gave noticeably inferior results concerning durability.

In contrast, it was found that thin films without film defects can be formed by using, as membrane materials, P-01 to P-09, which are polymers obtained using m-phenylenediamine compounds represented by General Formula (I) as raw materials. It was also found that, by using these thin films as gas separation layers, the permeation rate of carbon dioxide can be increased to 25 GPU or higher, while the gas separation selectivity ($R_{CO2}/R_{CH4}$) can also be increased to 20 or higher. That is, it can be seen that both gas permeability and gas separation selectivity can be realized at high levels. Furthermore, it was also found that in a case in which P-01 to P-09 were used as membrane materials, the membranes are not likely to be plasticized even if exposed to toluene and are capable of exhibiting high gas separation selectivity in a sustained manner.

As such, an m-phenylenediamine compound represented by General Formula (I) can impart desired characteristics or functionality to a polymer compound based on the characteristic molecular structure of the compound, in a case in which the compound is used as a raw material for the synthesis of the polymer compound.

EXPLANATION OF REFERENCES

1: gas separation layer
2: porous layer
3: nonwoven fabric layer
10: gas separation composite membrane

What is claimed is:

1. An m-phenylenediamine compound represented by General Formula (I),

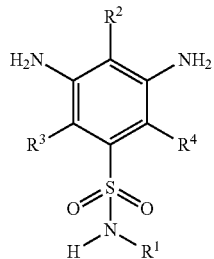

General Formula (I)

in the formula, $R^1$ represents a hydrogen atom, an alkyl group, a cycloalkyl group, or an aryl group; and $R^2$, $R^3$, and $R^4$ each represent an alkyl group.

2. An m-phenylenediamine compound represented by General Formula (II),

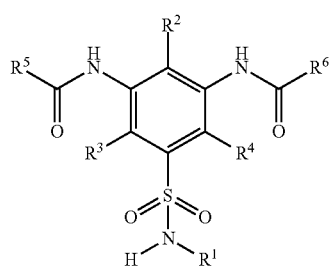

General Formula (II)

in the formula, $R^1$ represents a hydrogen atom, an alkyl group, a cycloalkyl group, or an aryl group; $R^2$, $R^3$, and $R^4$ each represent an alkyl group; and $R^5$ and $R^6$ each represent an alkyl group.

3. The m-phenylenediamine compound according to claim 2, wherein in General Formula (II), $R^5$ and $R^6$ each represent a trifluoromethyl group.

4. An m-phenylenediamine compound represented by General Formula (III),

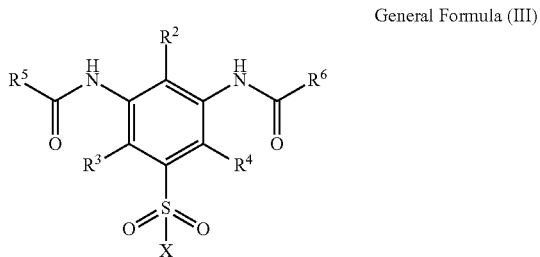

General Formula (III)

in the formula, $R^2$, $R^3$, and $R^4$ each represent an alkyl group; $R^5$ and $R^6$ each represent an alkyl group; and X represents a chlorine atom or a bromine atom.

5. The m-phenylenediamine compound according to claim 4, wherein in General Formula (III), $R^5$ and $R^6$ each represent a trifluoromethyl group.

6. The m-phenylenediamine compound according to claim 4, wherein in General Formula (III), X represents a chlorine atom.

7. The m-phenylenediamine compound according to claim 5, wherein in General Formula (III), X represents a chlorine atom.

8. A method for producing a polymer compound, the method comprising obtaining a polymer compound by using the m-phenylenediamine compound according to claim 1 as a raw material.

9. The method for producing a polymer compound according to claim 8, wherein the polymer compound is a compound selected from a polyimide compound, a polyurethane compound, a polyurea compound, and a polyamide compound.

* * * * *